(12) United States Patent
Lacombe et al.

(10) Patent No.: US 7,566,571 B2
(45) Date of Patent: Jul. 28, 2009

(54) DETECTION OF GELS IN A SOLUTION POLYMERIZATION

(75) Inventors: Yves Lacombe, Calgary (CA); Geoffrey Richard Harding, Calgary (CA)

(73) Assignee: Nova Chemicals (International) S.A. (CH)

( * ) Notice: Subject to any disclaimer, the term of this patent is extended or adjusted under 35 U.S.C. 154(b) by 805 days.

(21) Appl. No.: 11/143,407

(22) Filed: Jun. 2, 2005

(65) Prior Publication Data

US 2005/0277196 A1 Dec. 15, 2005

(30) Foreign Application Priority Data

Jun. 14, 2004 (CA) ................................ 2470887

(51) Int. Cl.
*G01N 33/44* (2006.01)
*G05B 21/00* (2006.01)

(52) U.S. Cl. ............................ 436/85; 436/55; 436/171; 700/266; 700/269

(58) Field of Classification Search .................. 436/171, 436/55, 85; 700/266, 268–269
See application file for complete search history.

(56) References Cited

U.S. PATENT DOCUMENTS 5,151,474 A 9/1992 Lange et al. ................... 526/60
6,072,576 A 6/2000 McDonald et al. .......... 356/300
6,153,873 A * 11/2000 Wolf ........................ 250/208.1

FOREIGN PATENT DOCUMENTS

CA 703704 2/1965

OTHER PUBLICATIONS

Chen et al., "Estimation of Polymerization Efficiency in nthe Formation of Polyacrylamide Gel, Using Continuous Otpicla Scanning During Polymerization", Journasl od Biochemical and Biophysical Methods, 1, 1979, p. 105-116.*
Jochen, C. E. et al, Powder Technology 2000, 108, 90-94.*
Reis, M. M. et al, Macromolecular Rapid Communications 2003, 24, 620-624.*

* cited by examiner

*Primary Examiner*—Arlen Soderquist
(74) *Attorney, Agent, or Firm*—Kenneth H Johnson

(57) ABSTRACT

In a solution polymerization process the increase in gel content in the solution at one or more locations may be detected by monitoring the structure of a spectrum obtained by analyzing the reaction at said one or more locations using a spectrometer selected from the group consisting of infrared spectrometers, near infrared spectrometers and Raman spectrometers.

8 Claims, 1 Drawing Sheet

DETECTION OF GELS IN A SOLUTION POLYMERIZATION

FIELD OF THE INVENTION

The present invention relates to a process to detect an increase in gels in a solution polymerization process. Gels are polymers having a higher molecular weight than the average or target molecular weight range for a product specification. More particularly the present invention is useful in detecting gel flurries during a solution polymerization process. Generally gels are insoluble in the target polymer and result in optical imperfections in films made from the resulting resin (e.g. fish eyes).

BACKGROUND OF THE INVENTION

In a solution polymerization process polymer is soluble in the hydrocarbyl solvent/diluent used for the process. At some locations or times in the process the polymer may come out of solution and the resulting polymer is generally difficult to re-dissolve in the solvent/diluent in the process. This polymer may have a different, typically higher, molecular weight and when the polymer is recovered from the process the gels tend to be separate resin particulates dispersed with in the main resin product.

There are a number of methods used to detect particles in a polymer. For example there are instruments to determine particle size distribution of or within a polymer sample. For example laser light scattering measurements are used in commercial equipment such as the Coulter™ LS230 or the Horeiba™ LA 910 particle size determination equipment. Generally these devices are used off line and the product is diluted in a solvent or diluent. Typically the procedure is conducted off line and it takes about 20 to 30 minutes to get the results. While the method is good for determining for example the particle size distribution within a latex or the size of rubber particles in a sample of high impact polystyrene resin the process is not suitable for in or on-line real time measurement during a polymerization.

U.S. Pat. No. 5,151,474 issued Sep. 29, 1992 to Lang et al., assigned to the Dow Chemicals Company teaches an on-line real time process to monitor the concentration of monomer and co monomer in a recycle stream during a solution polymerization process using Fourier transform infrared spectroscopy (FTIR). The patent fails to suggest the method could be used to detect gel flurries in the process. Further the process of the reference adsorption peaks are measured at specific wavelengths and not over the entire spectra.

U.S. Pat. No. 6,072,576 issued Jun. 6, 2000 in the name of McDonald et al., assigned to Exxon Chemical Patents Inc. teaches a process to control a number of reactions including polymerization in which a Fourier transform near infrared (FTNIR) spectra is used to control such a reaction to produce a product having a desired set of properties. A standard set of spectra for the desired product are obtained. The spectra are corrected for measurement errors (calibration curves). The corrected spectra are then weighted relative to an orthonormal base function. Then a value is obtained for each property of the calibration curves. Then determining a predictive model relating the value for the desired property to the set of weights (e.g. relating the spectra to the orthonormal base function). Then a spectra is obtained and an estimated value for the property is determined from the spectra and the difference between the value of the property and the value of the estimate is used to control the process (to return the value of the estimate to the value of the property). The present invention does not contemplate such a process. Rather it indirectly (via noise) measures the presence of gels in the solution of polymer in the process.

The present invention seeks to provide a simple in-line or on-line method to determine the presence of gel flurries in a solution polymerization process.

SUMMARY OF THE INVENTION

The present invention provides in a solution polymerization process the improvement of detecting the increase in gel content in the solution at one or more locations by monitoring the structure of a spectrum obtained by analyzing the stream (of reactants and solvent) at said one or more locations using a spectrometer selected from the group consisting of infrared spectrometers, near infrared spectrometers and Raman spectrometers.

DETAILED DESCRIPTION

Figure 1:
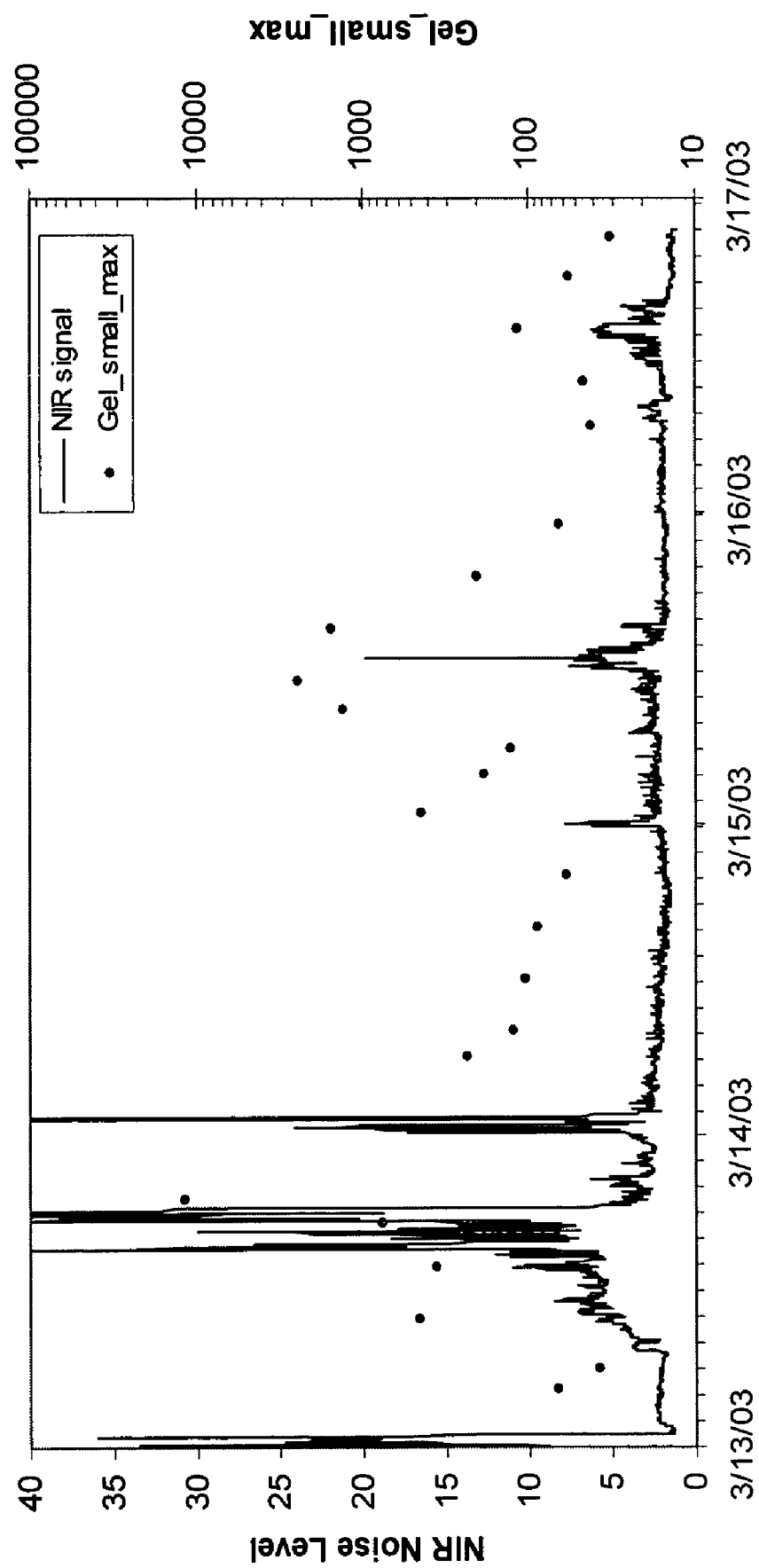
FIG. 1 is a comparison of in-line gel detection using a near infrared spectra and gel detection in a film made from the resulting resin.

Solution polymerization is a well-known technology. The monomers, typically a mixture of one or more $C_{2-8}$ alpha olefins are dissolved in a hydrocarbyl solvent. Typically the polymerization is a polymerization process for one or more $C_{2-8}$ olefins and the solvent is a $C_{4-8}$ aliphatic hydrocarbon.

In particular, the polymers of alpha olefins may be homopolymers of ethylene or copolymers of ethylene and higher alpha olefins i.e. alpha olefins especially such higher alpha olefins having 3 to 12 carbon atoms (i.e. $C_{3-12}$ alpha olefins), preferably having from 3 to 8 carbon atoms, examples of which are 1-butene, 1-hexene and 1-octene. The preferred higher alpha olefins have 4 to 10 carbon atoms. Optionally, cyclic endomethylenic dienes may be copolymerized with the ethylene and $C_{3-12}$ alpha olefins. Such polymers are known. Optionally, small amounts of hydrogen, for example 1-40 parts per million by weight, based on the total solution fed to the reactor may be added to one or more of the feed streams of the reactor system in order to improve control of the melt index and/or molecular weight distribution of the polymer and thus aid in the production of a more desirable product, as is disclosed in Canadian Patent 703,704.

Generally the monomer feed will comprise from 80 to 100 weight % of ethylene and from 20 to 0 weight % of one or more co monomers, preferably $C_{4-8}$ alpha olefins.

In the polymerization process the catalyst, inert hydrocarbon solvent monomer(s), and optionally hydrogen for control of the polymer molecular weight, are fed to a reactor system dissolved in the solvent.

The polymerization temperatures may be in, but not limited to, the range of 105° C. to 200° C. and especially in the range of 130° C. to 180° C. The polymerization process may be conducted in a reactor system such as in a tubular reactor a continuous stirred tank reactor (CSTR) which is typically jacketed for temperature control, or multi-reactor systems such as a chain of two or more CSTR's. The pressures used in the process of the present invention are those known for solution polymerization processes, for example, pressures in the range of about 4-20 MPa. Pressure and temperature are controlled so that the polymer formed tends to remain in solution. Problems arise when polymer comes out of solution.

The solvent used in the preparation of the coordination catalyst is an inert hydrocarbon. The hydrocarbon may be a $C_{4-8}$ hydrocarbon, preferably aliphatic hydrocarbon. Such solvents are known and include for example, hexane, heptane, octane, cyclohexane, methylcyclohexane and hydrogenated naphtha (e.g. such as ISOPAR™ sold by Exxon).

The process of the present invention is not limited to any particular type of catalyst. The catalyst may be a Ziegler Natta-type catalyst typically comprising a transition metal, such as a titanium halide or an alkyl or alkoxide titanium halide (e.g. $TiCl_3$, $TiCl_4$, $Ti((O_a)R)_b X_c$ where a is 0 or 1, R is a $C_{1-8}$ preferably $C_{1-4}$ alkyl compound X is a halide preferably chlorides and the sum of b and c is the valence of titanium), a magnesium halide which may be made in situ by reaction of a magnesium alkyl compound (e.g. $Mg (R^1)_d X_e$ where each $R^1$ is independently a $C_{1-8}$, preferably $C_{1-4}$ alkyl radical and the sum of d and e is 2, and a halide donor, typically a lower ($C_{1-8}$, preferably $C_{1-4}$) alkyl radical, an aluminum alkyl or an aluminum alkyl halide (e.g. trimethyl aluminum or diethyl aluminum chloride, tri n-hexyl aluminum; tri octyl aluminum) on a support such as silica or alumina and optionally containing an electron donor. These types of catalysts are typically activated with an aluminum alkyl or an aluminum alkyl halide compound. The catalyst may be a single site type catalyst such as the metallocenes of Exxon or the constrained geometry catalysts of Dow or the phosphinimine and ketimine catalyst of NOVA Chemicals. Generally such catalyst contain a at least one ligand which is a cyclopentadienyl or indenyl compound which is unsubstituted or substituted with a halogen atom, or a lower ($C_{1-8}$) alkyl radical (Cp type ligands), a bulky ligand such as an amido ligand or a phosphinimine or ketimine ligand and a leaving ligand such as a halogen or a lower ($C_{1-8}$) alkyl radical and which Cp-type ligands may be bridged or unbridged to the bulky ligand. These catalysts are typically activated with an aluminoxane compound (e.g. MAO—methyl alumoxane) or boron activators.

In accordance with the present invention a spectrometer may take the spectra of the solution at one or more locations in the polymerization process. The spectrum may be infrared, near infrared or Raman. Typically, the spectrum may be taken within (or over), the range from about 400 to 2,500 nanometers. This covers the region from near infrared through to visible. The spectrum need not cover the entire range but could cover discrete sections or portions of the range (e.g. visible, near IR or Raman ranges).

The spectrometers cells or probes could be mounted in-line on the reactor equipment (e.g. directly in the process line) or could be mounted on a parallel sampling section of small diameter pipe (e.g. on-line). In some cases on-line samples may require some conditioning or treatment prior to the spectra being taken. Preferably the spectrometer is mounted in-line on the reactor piping. The spectra may be transmittance spectra or diffuse reflectance spectra. The spectra may be obtained using a grating monochromotor. The spectra may be acquired using a Fourier transform infrared spectrometer. The spectra may be acquired using an acousto-optic tunable filter (AOTF) near infrared spectrometer.

Without being bound by theory it is believed the particles will be fairly small. From classical theory the particles being detected should have a particle size not less than about the smallest wavelength (e.g. 400 nanometers). Typically it is believed the particles may have a size from about 400 nanometers up to about 500 microns (the latter figure being based on the size of gel particles in film made from the polyethylene). Generally, the particle size may range from about 400 nanometers to 500 microns typically from about 400 nanometers up to about 400 microns, preferably from 400 nanometers to about 100 microns.

The spectrometers probes or cells (e.g. via optical fibers—note one spectrometer could service several locations using optical fibers) may be located at a number of locations. They may be at the exit of one or more reactors or at the exit to one or more heat exchangers used in the process.

The spectra may be stored in one or more micro-processors or computers. To detect a gel flurry at a time ($T_j$), a mathematical method is applied to spectrum $T_j$ to extract the features of the spectrum related to gels (mostly additional noise in the spectrum). The resulting spectrum is then "read" for noise. If there are no gel flurries the spectrum should be flat or near flat.

More particularly the process comprises the steps of:

(i) at an initial time $T_1$ taking a spectrum of the stream at said one or more locations;

(ii) at one or more subsequent times $T_j$ wherein $j$ is one or more times after $T_1$ taking one or more further spectra of the effluent stream at said one or more location;

(iii) using a mathematical method to extract features which correlate with gels from the spectrum and integrating the resulting spectrum to quantify the noise level. The mathematical method can be, but is not limited to, applying a high pass digital filter to the spectrum or subtracting the Exponential Moving Average (EMA) spectrum from spectrum $T_j$; and (iv) following the general tendency of the noise level over time.

It is also be possible to compare spectra from cells or probes located at different locations in the process at the same or about the same time to determine a likely source for the gel flurries. This is particularly true if the gels result from deposited polymer (e.g. polymer deposited on or in equipment such as heat exchangers or agitators) becoming dispersed within the reaction mixture. For example if the process used two or more CSTR's a spectrometer cell or probe could be at the exit of each reactor. Similarly a spectrometer cell or probe could be at the exit from heat exchangers and at the exit from one or more flash tanks in the process.

The solution passing from the polymerization reactor is normally treated to deactivate any catalyst remaining in the solution. A variety of catalyst deactivators are known, examples of which include but not limited to fatty acids, alkaline earth metal salts of aliphatic carboxylic acids and alcohols. The hydrocarbon solvent used for the deactivator is preferably the same as the solvent used in the polymerization process. If a different solvent is used, it must be compatible with the solvent used in the polymerization mixture and not cause adverse effects on the solvent recovery system associated with the polymerization process.

After deactivation of the catalyst, the solution containing polymer may be passed through a bed of activated alumina or bauxite, which removes part, or all of the deactivated catalyst residues. In a preferred embodiment, the polymerization is conducted without removal of deactivated catalyst residues. The solvent may then be flashed off from the polymer, which subsequently may be extruded into water and cut into pellets or other suitable comminuted shapes. The recovered polymer may then be treated with saturated steam at atmospheric pressure to, for example, reduce the amount of volatile materials and improve polymer color. The treatment may be carried out for about 1 to 16 hours, following which the polymer may be dried and cooled with a stream of air for 1 to 4 hours.

Pigments, antioxidants, UV screeners, hindered amine light stabilizers and other additives may be added to the polymer either before or after the polymer is initially formed into pellets or other comminuted shapes. The antioxidant incorporated into polymer obtained from the process of the present invention may, in embodiments, be a single antioxidant e.g. a hindered phenolic antioxidant, or a mixture of antioxidants e.g. a hindered phenolic antioxidant combined with a secondary antioxidant e.g. a phosphite. Both types of antioxidant are known in the art. For example, the ratio of phenolic antioxidant to secondary antioxidant may be in the range of 0.1:1 to 5:1 with the total amount of antioxidant being in the range of 200 to 3,000 ppm.

The polymerization process of the present invention may be used to prepare homopolymers of ethylene and copolymers of ethylene and higher alpha-olefins having densities in the range of, for example, about 0.900-0.970 g/cm$^3$ and especially 0.910-0.930 g/cm$^3$. Such polymers may have a melt index, as measured by the method of ASTM D-1238, condition E, in the range of, for example, about 0.1-200 dg/min, and especially in the range of about 0.30-45 dg/min. Such a melt index tends to indicate a higher molecular weight of the resulting polymer. The polymers may be manufactured with narrow or broad molecular weight distribution. For example, the polymers may have a stress exponent, a measure of molecular weight distribution, in the range of about 1.1-2.5 and especially in the range of about 1.3-2.0. The process of the invention is believed to be particularly useful in the manufacture of broad molecular distribution polymers.

Stress exponent is determined by measuring the throughput of a melt indexer at two stresses (2,160 g and 6,480 g loading) using the procedures of the ASTM melt index test method, and the following formula:

Stress exponent=1/0.477×log (wt. of polymer extruded with 6480 g wt.)/(wt. of polymer extruded with 2160 g wt.)

Stress exponent values of less than about 1.40 indicate narrow molecular weight distribution while values above about 1.70 indicate broad molecular weight distribution.

EXAMPLE 1

NIR spectrometer probes or cells were installed at the exit of the continuous stirred reactors of NOVA Chemicals solution phase demonstration plant at Sarnia, Ontario. Ethylene octene copolymers were made in a lower alkyl hydrocarbon solvent in the presence of a Ziegler Natta catalyst at a temperature in the range from about 200 to 250° C. at moderate pressures. During a 5 day run period form Mar. 13 to Mar. 17, 2003 the process of the present invention was used to detect gels leaving the CSTR. NIR spectra were collected continuously at an interval of 2 minutes during the 5 day run period. A high-pass digital filter was applied to each spectrum to extract the noise component of the signal. The resulting spectra were integrated to give a noise level. Samples of the resulting polymer made during these runs were made into film and the films were evaluated using a gel camera for the presence of gel particles. FIG. 1 is a plot of the noise of the near IR spectrum and the gel evaluations in the films made using the resins. There is a good correlation between the spectra noise determined in accordance with the present invention and the gel levels in the resulting films.

What is claimed is:

1. In a solution polymerization process the improvement of detecting the increase in the content of gels having a particle size from 400 nanometers to 400 microns in the solution at one or more locations comprising the steps of:
   (i) at an initial time $T_1$ acquiring an infrared, near infrared or a Raman transmittance or diffuse reflectance spectrum within a wavelength range from 400 to 2,500 nanometers of the solution at said one or more locations;
   (ii) at one or more subsequent times $T_j$ wherein j is one or more times after $T_1$ acquiring one or more further infrared, near infrared or Raman transmittance or diffuse spectra within a wavelength range from 400 to 2,500 nanometers of the solution at said one or more locations;
   (iii) using a mathematical method selected from the group consisting of applying a high pass digital filter to the spectrum taken at $T_j$ or subtracting the Exponential Moving average (EMA) from the spectrum taken at $T_j$ and integrating the resulting spectrum to quantify the noise level; and
   (iv) following the general tendency of the noise level over time.

2. The process according to claim 1, which is a continuous process and the spectrometer is in-line or on-line.

3. The process according to claim 2, wherein the spectrum is acquired using a Fourier transform near infrared spectrometer (FTNIR).

4. The process according to claim 2, wherein the spectrum is acquired using a grating monochromator near infrared spectrometer.

5. The process according to claim 2, wherein the spectrum is acquired using an acousto-optic tunable filter (AOTF) near infrared spectrometer.

6. The process according to claim 2, in which the reaction takes place in two reactors and the gel level is detected at the exit for each reactor.

7. The process according to claim 6, wherein in the polymerization is a polymerization process for one or more $C_{2-8}$ olefins and the solvent is a $C_{4-8}$ aliphatic hydrocarbon.

8. The process according to claim 7, wherein the $C_{2-8}$ olefins comprise from 100 to 80 weight % of ethylene and from 0 to 20 weight % of one or more $C_{4-8}$ alpha olefins.

* * * * *